United States Patent [19]

Hoffmann et al.

[11] Patent Number: 5,651,886

[45] Date of Patent: Jul. 29, 1997

[54] SEPARATION COLUMN FOR CHROMATOGRAPHY

[75] Inventors: Bernd-Walter Hoffmann; Guenter Schaeufele, both of Karlsruhe, Germany

[73] Assignee: Hewlett-Packard Company, Palo Alto, Calif.

[21] Appl. No.: 641,085

[22] Filed: Apr. 29, 1996

Related U.S. Application Data

[63] Continuation of Ser. No. 404,039, Mar. 14, 1995, abandoned.

[30] Foreign Application Priority Data

Mar. 30, 1994 [DE] Germany ............................ 9405378 U

[51] Int. Cl.[6] .................................................. B01D 15/08
[52] U.S. Cl. ........................ 210/198.2; 210/656; 96/101
[58] Field of Search .......................... 210/198.2, 496, 210/497.01, 500.25, 500.26, 510.1, 656; 96/101

[56] References Cited

U.S. PATENT DOCUMENTS

| | | | |
|---|---|---|---|
| 2,723,756 | 11/1955 | Miller | 210/198.2 |
| 3,677,410 | 7/1972 | Okumura | 210/198.2 |
| 3,856,681 | 12/1974 | Huber | 210/198.2 |
| 3,954,608 | 5/1976 | Valentin | 210/198.2 |
| 4,107,041 | 8/1978 | Karlson | 210/198.2 |
| 4,138,336 | 2/1979 | Mendel | 210/198.2 |
| 4,208,284 | 6/1980 | Pretorius | 210/198.2 |
| 4,486,312 | 12/1984 | Slingsby | 210/198.2 |
| 4,496,461 | 1/1985 | Leeke | 210/198.2 |
| 4,508,624 | 4/1985 | Nagata | 210/658 |
| 4,675,104 | 6/1987 | Rai | 210/198.2 |
| 4,676,898 | 6/1987 | Saxena | 210/198.2 |
| 4,693,985 | 9/1987 | Degen | 210/198.2 |
| 4,694,682 | 9/1987 | Heikkila | 210/198.2 |
| 4,793,920 | 12/1988 | Cortes | 210/198.2 |
| 4,946,592 | 8/1990 | Galaj | 210/500.25 |
| 5,104,546 | 4/1992 | Filson | 210/500.25 |
| 5,110,470 | 5/1992 | Yokosawa | 210/500.25 |
| 5,141,634 | 8/1992 | Carr | 210/198.2 |
| 5,253,981 | 10/1993 | Yang | 210/198.2 |
| 5,269,926 | 12/1993 | Webster | 210/500.25 |
| 5,405,529 | 4/1995 | Shimai | 210/500.25 |

FOREIGN PATENT DOCUMENTS

| | | | |
|---|---|---|---|
| 29 30 585 A1 | 2/1980 | Germany | 210/198.2 |
| 41 12 258 A1 | 10/1992 | Germany | 210/198.2 |
| 41 18 785 A1 | 12/1992 | Germany | 210/198.2 |
| 4404291 A1 | 8/1994 | Germany | 210/198.2 |

OTHER PUBLICATIONS

Patent Abstract of Japan, P–577, May 19, 1987, vol. 11, No. 153.
Diceron–Products, DIDIER, 6 pages, Sep. 1991.
Zirconium Oxide In Engineering Ceramics, 3 pages, Sep. 1991.
Snyder, Introduction to Modern Liquid Chromatography, John Wiley & Sons, 1979, New York, pp. 203–204.

*Primary Examiner*—Ernest G. Therkorn

[57] ABSTRACT

A separation column for chromatography, such as for liquid chromatography or supercritical fluid chromatography, comprises a separation tube made of a ceramic composite material and a stationary phase packed into the separation tube. The column has a high pressure stability and smooth inner surface leading to improved chromatographic properties.

4 Claims, 1 Drawing Sheet

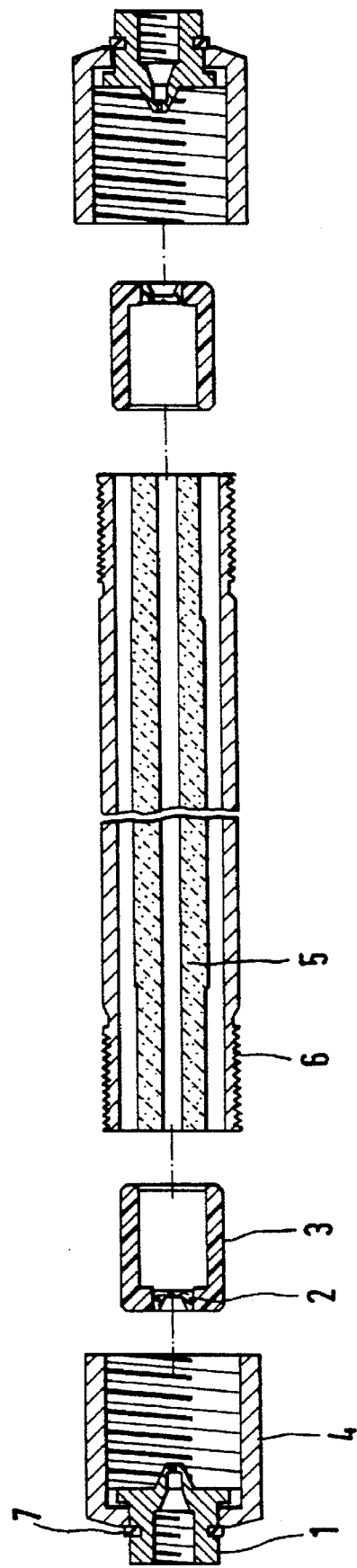

SEPARATION COLUMN FOR CHROMATOGRAPHY

This is a continuation of application Ser. No. 08/404,039 filed on Mar. 14, 1995, now abandoned.

The invention relates to a separation column for chromatography. Such separation columns are used in high performance liquid chromatography or supercritical fluid chromatography (SFC), for example.

BACKGROUND OF THE INVENTION

The separation columns commonly used in liquid chromatography and supercritical fluid chromatography consist essentially of a tube filled with solid particles forming the stationary phase. This packed column is equipped at both ends with special fittings, via which it can be connected to the analytical measuring instrument, such as the chromatograph. During operation, such columns are typically subjected to high pressures of up to 400 bar.

Current separation columns for chromatography usually consist of a stainless steel tube in which the stationary phase is packed. The stationary phase is retained at each end of the stainless steel tube by a sieve or frit. Furthermore, fittings, typically also of stainless steel, are provided at the ends. An example of a separation column in the art is disclosed in U.S. Pat. No. 4,737,284.

In addition to the stationary phase, the surface quality of the tube inside wall is especially important for the chromatographic behavior and service life of the separation column. If the surface is not sufficiently smooth and homogeneous, this adversely affects the flow behavior of the sample substances undergoing separation by passing through the column. In particular, variations in local flow rates can occur in the tube, causing asymmetry in the chromatographic peaks. As a result, quantitative analysis is impeded or subjected to errors. Due to the stringent requirements placed on the surface quality of the tube inside wall, conventional chromatographic tubes are expensive.

An additional limitation of stainless steel columns arises under extreme conditions with respect to pH and the type of mobile phase. Polymer stationary phases are now available that permit chromatographic separations across the entire pH range from strongly acidic (<pH 3) to strongly basic (pH 12-13). Varying the pH range permits, for example, acidic or basic substances to be transformed to their conjugate molecular structure and then analyzed using reversed-phase chromatography as a neutral molecule without further additive in the mobile phase. Although polymer phases, in contrast to silica gel phases, have extended the working range by allowing the use of strongly acidic/basic mobile phases, the corrosive action on stainless steel tubes under these conditions remains a disadvantage in practical use.

As the sample substances increase in complexity, increasingly complex separation methods/conditions are required; stainless steel columns are not always satisfactory under these conditions, such as under high concentrations of oxidating salts in the mobile phase.

Moreover, problems can arise with stainless steel columns if there are samples to be analyzed that interact chemically with the stainless steel. The stainless steel material, which, as is well known, is manufactured from a melt of different metal ions, can act as a Lewis acid, which can form metal chelates with certain sample substances such as b-diketones, dihydroxy-naphthalene compounds, or various heterocyclic compounds.

In addition to stainless steel, other tube materials have proven themselves, primarily for bioanalytical applications. Such materials are:

stainless steel with a glass-coated inner surface, polyetheretherketone (PEEK), polytetrafluoroethylene (PTFE), and borosilicate glass.

For example, DE-A-2 930 962 discloses a separation column with a glass tube. The cited tubes do not resolve all problems occurring with stainless steel columns, however. Furthermore, they fail to offer the special advantages of stainless steel tubes. In particular, they lack pressure stability under the high pressures common in chromatography of up to 400 bar during chromatographic analysis and up to 1000 bar during the packing process. Moreover, glass is fragile and plastic can swell when using certain mobile phases such as tetrahydrofuran (THF).

SUMMARY OF THE INVENTION

Compared to the state of the art, it is an object of the invention to provide a separation column for chromatography that avoids the cited problems of existing separation columns. In particular, the invention provides a solution to the object of providing a separation column that does not exhibit the cited limitations of stainless steel columns but does retain their advantages, primarily their pressure stability.

The solution of the mentioned object is stated in claim 1. In accordance with a fundamental principle of the invention, the separation tube, which contains the stationary phase, is made from ceramic composite material. The ceramic composite material has a particularly high pressure stability. It can be produced from a ceramic base material by admixture of an oxidic material, for example.

The invention has the following additional advantages:

The ceramic material does not corrode and is chemically inert. The tube material does not interact with the sample substances or the mobile phase. The column can be used across the entire pH range without being subjected to chemical corrosion. The column can be used for bioanalytical applications.

The column of the invention has high stability, allowing it to easily withstand the high pressures common in chromatography. The ceramic tube can be manufactured without additional treatment or processing of the inside wall surface; in particular, it is a significant advantage that polishing of the inside wall is not required. Due to the high degree of smoothness and evenness of the tube inside wall, the column of the invention has excellent chromatographic properties, which surpass even those of highly-polished stainless steel. A further advantage of the invention lies in the column's low cost of manufacture. Due to the high degree of smoothness and stability of the tube inside wall surface, the column can be repacked many (at least 10) times without requiring repolishing of the tube inside wall. This contributes to a significant cost reduction. Furthermore, the simple recyclability of the tube into the process for manufacturing a new packed column is significant from an environmental standpoint.

As previously mentioned, an important advantage of the invention lies in the homogeneity and smoothness of the inside wall surface of the tube. Very good chromatographic properties are attainable without polishing the inside surface. Of course, the ceramic material surface can also be polished, if this should prove desirable in certain cases to achieve an even smoother surface. With known stainless steel tubes, maintaining the necessary tube quality requires a refinishing of the inside wall when the column is repacked after the spent contents are removed. This is not only expensive but also leads to an enlargement of the tube inside diameter after repeated recycling. If refinishing is not conducted, the separation efficiency is reduced; furthermore, the service life of the packed column is shortened, since the packed bed can settle under pressure as a result of unevenness in the wall. All these disadvantages are avoided with the present invention.

A further benefit of the invention is that the thermal conductivity and heat capacity of ceramic composite materials are lower than those of stainless steel. In a practical embodiment of the invention, the thermal conductivity is at least 7 times lower and the specific heat capacity at least 20% less than those of stainless steel. As a result, a separation column in accordance with the invention is more resistant to unwanted thermal disturbances acting on the column from the outside during the chromatographic process. Furthermore, the thermal equilibrium process between the stationary and mobile phases is accelerated due to lower heat loss through the ceramic tube. Since this behavior is fundamentally conducive to a selective temperature change, the invention enables chromatographic separations to be conducted at different temperatures with high accuracy and without special effort to maintain the equipment at constant temperature.

Individual examples of materials yielding particularly advantageous results are given in the subclaims.

The following describes one embodiment of the invention with reference to the drawing. The drawing shows the component parts of a chromatographic column in the disassembled state.

DETAILED DESCRIPTION OF THE INVENTION

The key component of the column is ceramic separation tube 5. Column support 6 is positioned concentrically to separation tube 5. This support is made of stainless steel, for example. In the assembled state, sleeve 3 is positioned between separation tube 5 and column support 6. In one embodiment of the invention, sleeve 3 is made of plastic.

Filter element 2 with integrated seal is embedded in the face of sleeve 3. The purpose of this filter/seal element is to prevent impurities from entering the tube that either arise from system-related abrasion or are contained in the liquid being analyzed. In the assembled state, sleeve 3 is shrunk onto ceramic tube 5. Thrust piece I is inserted in sleeve 3 in the assembled state and secured to column support 6 by union nut 4. For this purpose, the end of the column support has a male thread. Thrust piece 1 is made of stainless steel, for example. Clamping ring 7 on thrust piece 1 secures the thrust piece to union nut 4.

As shown in the drawing, the previously described components, i.e., sleeve with filter element and seal, thrust piece, and union nut are also present at the other end of ceramic tube 5. These components are connected to ceramic tube 5 like those at the other end. The interior of tube 5 is packed with the stationary phase, for example with silica gel, modified silica gels (so-called reversed-phase materials), or ion exchangers. Furthermore, the entire spectrum of chromatographic carrier materials can be used. The assembled separation column can then be incorporated in a conventional manner into a liquid chromatograph or a supercritical fluid chromatograph.

An important feature of the invention is that tube 5 is made of a ceramic compound. One possible ceramic material is zirconium oxide ($ZrO_2$), with which a certain amount of another oxidic material has been admixed. An example of such an oxidic material is yttrium oxide ($Y_2O_3$). In a practical embodiment of the invention, approx. 5.1±0.15 percent by weight yttrium oxide was admixed. This additional oxidic material increases the stability of the ceramic. The resultant ceramic composite material is distinguished by its high stability, its resistance to chemicals, and its thermal properties.

In manufacturing the ceramic tube, control of the purity of the starting material as well as its particle size is important in avoiding pores on the ceramic surface or within the ceramic compound. Such pores would adversely affect the chromatographic behavior and the stability of the column. The cited control measures can employ optical methods such as image evaluation or electrical methods such as the disturbance of an electrical field (Coulter counter). In manufacturing the ceramic tube, ceramic powder is introduced into a cylinder, in the center of which is a mandrel with a very smooth surface. The powder is pressed isostatically and is also heated. The mandrel is then removed, resulting in a transfer of the surface quality of the mandrel to the ceramic material.

The ceramic tube can be produced in different lengths, diameters, and with various fittings to suit the desired chromatographic conditions. Furthermore, the tube can have male or female threads. In the embodiment shown in the drawing, tube 5 has a length of 120 mm, an inside diameter of 1.8 mm, and an outside diameter of 7.5 mm.

Cylindrical sleeve 3, which is shrunk onto each end of the ceramic tube, is a fluoroplastic or a comparable plastic material, such as PEEK. Alternatively, the plastic components can also be cemented to the ceramic tube. The packed column is sealed using conical thrust piece 1, the shape of which conforms to the plastic seal of filter element 2, allowing for the prescribed tolerances. The seal material is preferably a fluoroplastic. To attain an optimal connection between the ceramic tube and the sleeve, the ceramic tube itself can take various forms, for example flat on one or both ends or with an insert of appropriate length and diameter.

In addition to the previously mentioned zirconium oxide, ceramic materials for the invention can include other oxidic ceramics, such as aluminum oxide. Zirconium oxide, however, is generally more resistant chemically. In addition to yttrium oxide, the oxidic material admixed to produce a ceramic composite material can also be magnesium oxide (MgO) or cerium oxide. Typical concentrations of such admixtures are approx. 5 percent by weight. Yttrium oxide, however, has proven advantageous with respect to pressure stability.

We claim:

1. Separation column for chromatography with a separation tube and a stationary phase packed into the separation tube, wherein the separation tube is comprised of a ceramic composite material consisting essentially of a ceramic oxide with an admixture of a different oxidic material selected from the group consisting of Yttrium Oxide, Magnesium Oxide and Cerium Oxide, for providing stability to the separation tube under pressurized operating conditions, said ceramic composite material having a surface smoothness of a mandrel, said surface smoothness created by isostatically pressing said ceramic composite material about said mandrel to create said separation tube.

2. Separation column in accordance with claim 1, wherein the oxidic material contains yttrium oxide.

3. Separation column in accordance with claim 1, wherein the ceramic oxide contains zirconium oxide.

4. Separation column in accordance with claim 1, wherein the separation column is for liquid chromatography or supercritical chromatography.

* * * * *